United States Patent
Griggio et al.

(10) Patent No.: US 8,550,626 B2
(45) Date of Patent: Oct. 8, 2013

(54) INSTRUMENT FOR EYE EXAMINATION

(75) Inventors: Paola Griggio, Padua (IT); Fabio Turra, Padua (IT)

(73) Assignee: Centervue S.p.A., Padua (IT)

( * ) Notice: Subject to any disclaimer, the term of this patent is extended or adjusted under 35 U.S.C. 154(b) by 51 days.

(21) Appl. No.: 13/260,014

(22) PCT Filed: Apr. 1, 2009

(86) PCT No.: PCT/IT2009/000135
§ 371 (c)(1),
(2), (4) Date: Nov. 10, 2011

(87) PCT Pub. No.: WO2010/113193
PCT Pub. Date: Oct. 7, 2010

(65) Prior Publication Data
US 2012/0062842 A1    Mar. 15, 2012

(51) Int. Cl.
*A61B 3/14* (2006.01)
*A61B 3/10* (2006.01)

(52) U.S. Cl.
USPC ............ 351/206; 351/211; 351/214; 351/221

(58) Field of Classification Search
USPC ................................ 351/200–246
See application file for complete search history.

(56) References Cited

U.S. PATENT DOCUMENTS

| | | | |
|---|---|---|---|
| 4,279,478 A * | 7/1981 | Matsumura | 351/206 |
| 6,454,411 B1 * | 9/2002 | Trumbull | 351/211 |
| 7,347,552 B2 | 3/2008 | Reis | |
| 2004/0196432 A1 * | 10/2004 | Su et al. | 351/206 |
| 2007/0291277 A1 | 12/2007 | Everett et al. | |

FOREIGN PATENT DOCUMENTS

| | | |
|---|---|---|
| EP | 0363610 A1 | 4/1990 |
| EP | 1340451 A2 | 9/2003 |
| GB | 2359375 A | 8/2001 |
| JP | 2005-102946 A | 4/2005 |

OTHER PUBLICATIONS

Rainer Schuhmann et al., "Telezentrische Systeme für die optische Meβ und Prüftechnik," Technisches Messen 65 (1998) 4.

* cited by examiner

*Primary Examiner* — Mohammed Hasan
(74) *Attorney, Agent, or Firm* — Novak Druce Connolly Bove + Quigg LLP

(57) ABSTRACT

The present invention relates to an instrument for eye (E) examination, the system including an imaging system (2) to produce images of a portion of the eye to be examined; a projection system (3) to project a stimulus of visible light on a location in the portion of the eye to be examined and a background light on the portion of the eye to be examined; in which the projection system (3) has a telecentric design to uniformly project the stimulus and the background and includes a light source (114) and a movable mirror (112) which is moved according to the location of stimulus projection.

21 Claims, 9 Drawing Sheets

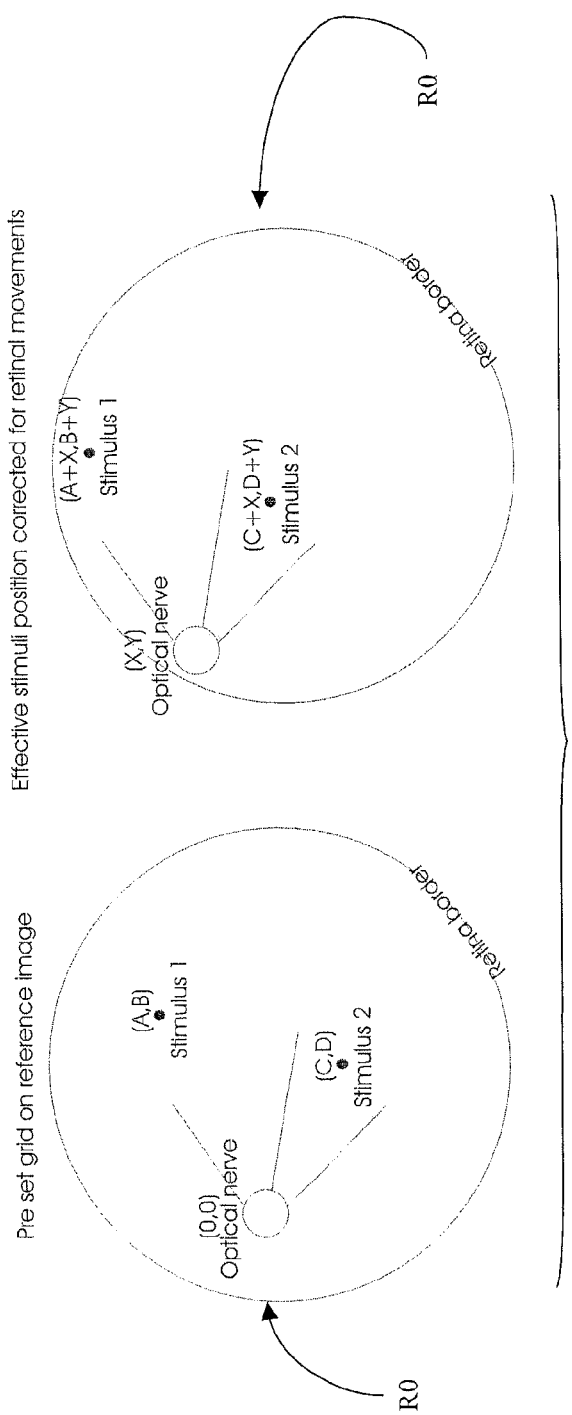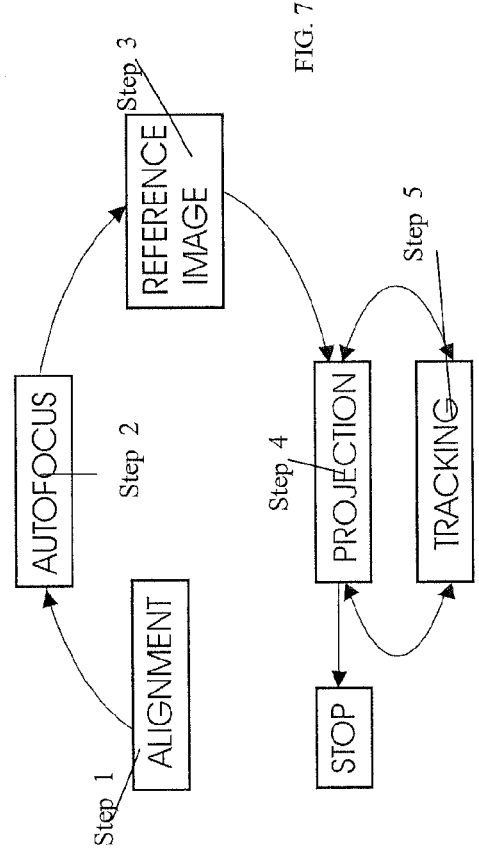
FIG. 8
FIG. 7

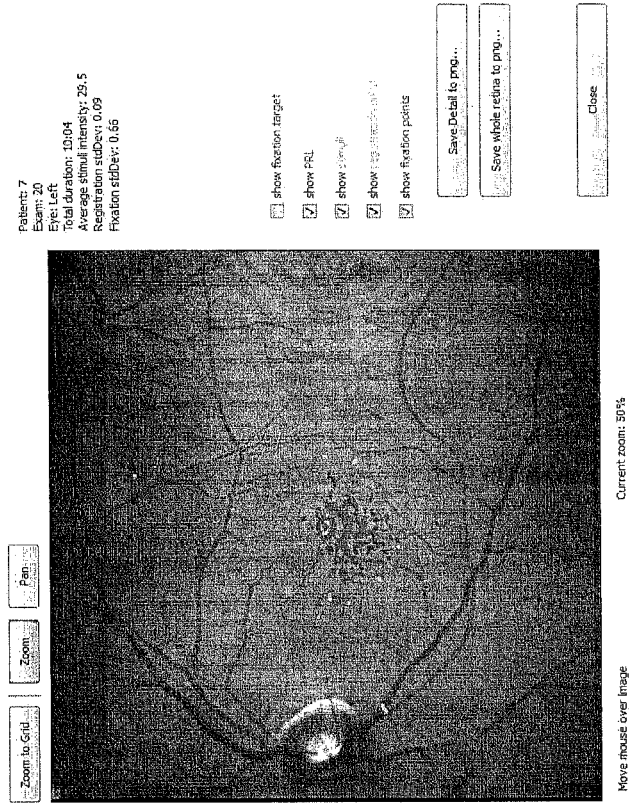
FIG. 11a
FIG. 11b
FIG. 12
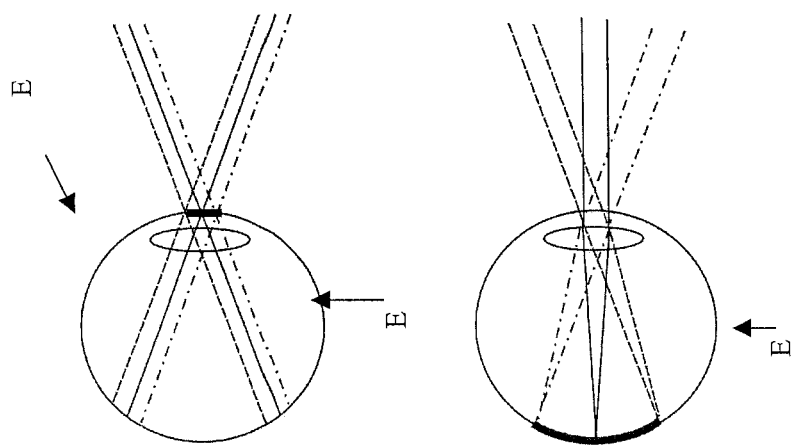

INSTRUMENT FOR EYE EXAMINATION

CROSS-REFERENCE TO RELATED APPLICATIONS

This application is a 35 U.S.C. 371 National Stage Application of International Application No. PCT/IT2009/000135, the entire contents of which are incorporated herein by reference in its entirety.

TECHNICAL FIELD

The present invention relates to an instrument for eye examination, and in particular, but not exclusively, for retina examination, of the type including the characteristics specified in the preamble to main claim 1.

TECHNOLOGICAL BACKGROUND

In the examination of the human eyes, in particular of the retinas of the same, fundus imaging is an essential tool. For this purpose, Scanning Laser Ophthalmoscopes (SLO) have been recently developed in order to rapidly obtain high resolution images of the ocular fundus and its internal structures.

Among the possible tests that a SLO may perform, the assessment of the function of the macular area of the human retina, in order to detect presence of any macular degeneration, preferably in its early stages, is an extremely important one, in order to obtain an indication on whether the macular function is normal, suspect or abnormal.

Generally, the assessment above described is obtained acquiring both images of the retinas of the patient and a more subjective assessment of the retinas' functionality projecting on the patient's retinas different stimuli.

U.S. Pat. No. 5,568,208 in the name of Frans J. Van de Velde discloses a modified laser ophthalmoscope which expands the range of clinical applications of the conventional scanning laser ophthalmoscope, being able of presenting the scanning laser raster with graphics to the retina and simultaneously allowing the observation of the anterior segment on the display monitor. The device, including a beam splitter, infrared light source, scanning laser ophthalmoscope, CCD camera, and optical filters, determines unambiguously in real-time the entrance pupil of the Maxwellian view scanning laser ophthalmoscope. The location of the entrance pupil and stimulus position on the retina can be moved independently.

Applicants have noted that the stimuli and the background projected onto the retina are not independent one from the other.

U.S. Pat. No. 6,705,726 in the name of Nidek Co., Ltd. relates to a novel instrument for the examination of the eye, namely the retina. The instrument features a LCD display for projection of various types of patterns and stimuli via an optical system onto the retina. The retina can be visualized by live IR image sequences as well as by visible light still frame images. It combines five examination types within one instrument, namely a perimetry examination, a microperimetry examination, a fixation stability examination, a scotoma boundary detection and psychophysical examinations.

Applicants have noted that the presence of an LCD to produce the stimuli limits the possibility of determining their location to a discrete number of "points" which depends on the pixel of the LCD screen.

U.S. Pat. No. 7,284,859 in the name of Physical Sciences, Inc., discloses a system and a method for providing a line-scanning laser ophthalmoscope (LSLO). The LSLO uses a substantially point source of light, such as infrared laser or a super-luminescent diode. The point source is expanded to a line. The LSLO scans the line of light in a direction perpendicular to a line across a region of an eye having an undilated pupil. The reflected light is received confocally, using monostatic beam geometry. A beam separator, such as a turning prism or a mirror, diverts one of the incoming light and the reflected light to separate the lights. An optical stop prevents non-confocally received light from reaching a one-dimensional detector, such as a linear CCD array. An electrical signal responsive to the output light at each of a plurality of locations along the line of output light is processed to provide images of the scanned portion of the eye.

SUMMARY OF THE INVENTION

The invention relates to an instrument for eye examination, in particular, but not limited, to a Scanning Laser Ophthalmoscope (SLO).

One of the main goal of the invention is to provide an instrument capable of furnishing an indication of the functionalities of the retina, in particular of its macular region, and to assess whether they are within so called "normal", "suspect" or "abnormal" ranges, according to statistical data. The retinas' functionalities are checked by means of a perimetric approach together with the acquisition of images of the retina using a microscope. This goal is achieved with an instrument for eye examination according to the invention which is compact, relatively cheap and at the same time includes a precise and effective projection system.

The instrument for eye examination of the invention permits to obtain a subjective measurement of the differential light sensitivity of the patient's paramacular area and an objective evaluation of the patient's ability to fixate: these tests are performed during a morphological monitoring of the macular area with light at a fixed wavelength, preferably infrared (IR) light.

The subjective macular sensitivity is determined by projecting stimuli of variable intensities and positions over an uniform background and verifying the response of the patient (the stimulus is either seen or not seen). The high precision of the sensitivity measurement is provided by the continuous monitoring of the retina which is preferably continuously tracked with a confocal system, as better outlined below.

The instrument of the invention includes an imaging system to obtain images of the retina, system which is preferably a laser scanning optical system in which a beam of light is focused by appropriate optics at a retina plane, and even more preferably a line-scanning laser optical system, for example the scanning system described in the U.S. Pat. No. 7,284,859, in which a substantially point source of light is transformed by proper optics into a line of light which scans a portion of the retina of the patient.

Preferably, the source of light is a source of IR light.

The reflected light is confocally received from the illuminated portion of the retina and provides an output light in a line focus configuration. Combining several output lines, an image of the retina is obtained, for example using a suitable camera.

Preferably a Maxwellian view illumination is used in the imaging system of the instrument of the invention.

This confocal IR imaging system allows sharp images to be continuously captured from the retina in order to evaluate presence/absence of morphological abnormalities. The small pupil size required for the illumination/imaging and which is determined by the optics of the instrument of the invention, thanks, among others, to the Maxwellian design, is an advantage (there is no need of using drops to enlarge the pupil's size of the patient) as well as the lack of uncomfortable flashes during the exam. The IR image is in fact accurate enough to provide morphological information that no additional color pictures need to be taken.

Additionally, the imaging system of the invention is confocal only in one direction, being a line scanning system, and not in the direction perpendicular to it: this allows cheaper optics maintaining at the same time a very good optical image resolution compared to the standard fundus camera and almost similar to the laser scanning system which are confocal in both directions.

According to a particular characteristic of the invention, the instrument further includes a projection system, to project onto the retina different stimuli in different locations.

The projection system has a telecentric design which guarantees a uniform illumination over the whole projection region with no dependence on the projection angle. Therefore the stimuli appear on the retina the same regardless of the projection angle.

The correct location of each stimulus on the retina is obtained by a movable mirror, preferably either a kinematic mounting mirror or a gimbal mounting mirror, driven by an appropriate software. The mirror projects onto the retina the stimuli, stimuli which are generated by a suitable light source, such as a LED light source, in a telecentric way, as already mentioned. LEDs are the preferred source because they can be very easily dimmed by pulse width modulation (PWM) and provide a stable output power. Moreover, they are poorly affected by aging and have a long lifetime. Other sources like fluorescent tubes or incandescent light bulbs may yield to calibration issues because their brightness is affected by driving voltage and by temperature and they suffer from aging effects.

Moreover, also the projection system has a Maxwellian design, so that the retina irradiance is not affected by the patients' pupil: the instrument exit pupil is designed to be much smaller than that of the patient and this guarantees an irradiance on the retina independent on the patient's pupil dynamic.

The imaging system and the projection system of the instrument of the invention are located on an optical head. The instrument further includes a control board to drive the optical head and a computer system, which drives the control board, accept commands from an user and hosts the software which control the overall functioning of the instrument.

Preferably, the output of the instrument of the invention is almost automatic: after the tests of the visualization of stimuli on the patient's retinas, the instrument of the invention displays a suitable graphic(s) in order to show the retinas functionalities classified in different ranges depending on the comparison with collected statistical data.

These objects and others, which will become clear from the following description, are achieved by the invention with an instrument for eye examination obtained in accordance with the appended claims.

BRIEF DESCRIPTION OF THE DRAWINGS

Further features and advantages of an instrument for eye examination according to the invention will become more clearly apparent from the following detailed description thereof, given with reference to the accompanying drawings, where:

FIG. 7 is a schematic diagram of the steps executed by a software included in the instrument of the invention;

FIG. 8 is a schematic simplified view of the computation of the shift of the patient's retina performed by an algorithm for retina tracking included in the software of FIG. 7;

FIGS. 11a and 11b are an upper view and a side view, respectively, of an eye E under examination using the instrument of the invention;

FIG. 12 represents another interface displayed on a screen in the instrument of the invention and summarizing additional results of a test performed with the instrument of FIG. 1 or FIG. 2.

PREFERRED EMBODIMENTS OF THE INVENTION

Figure 1:
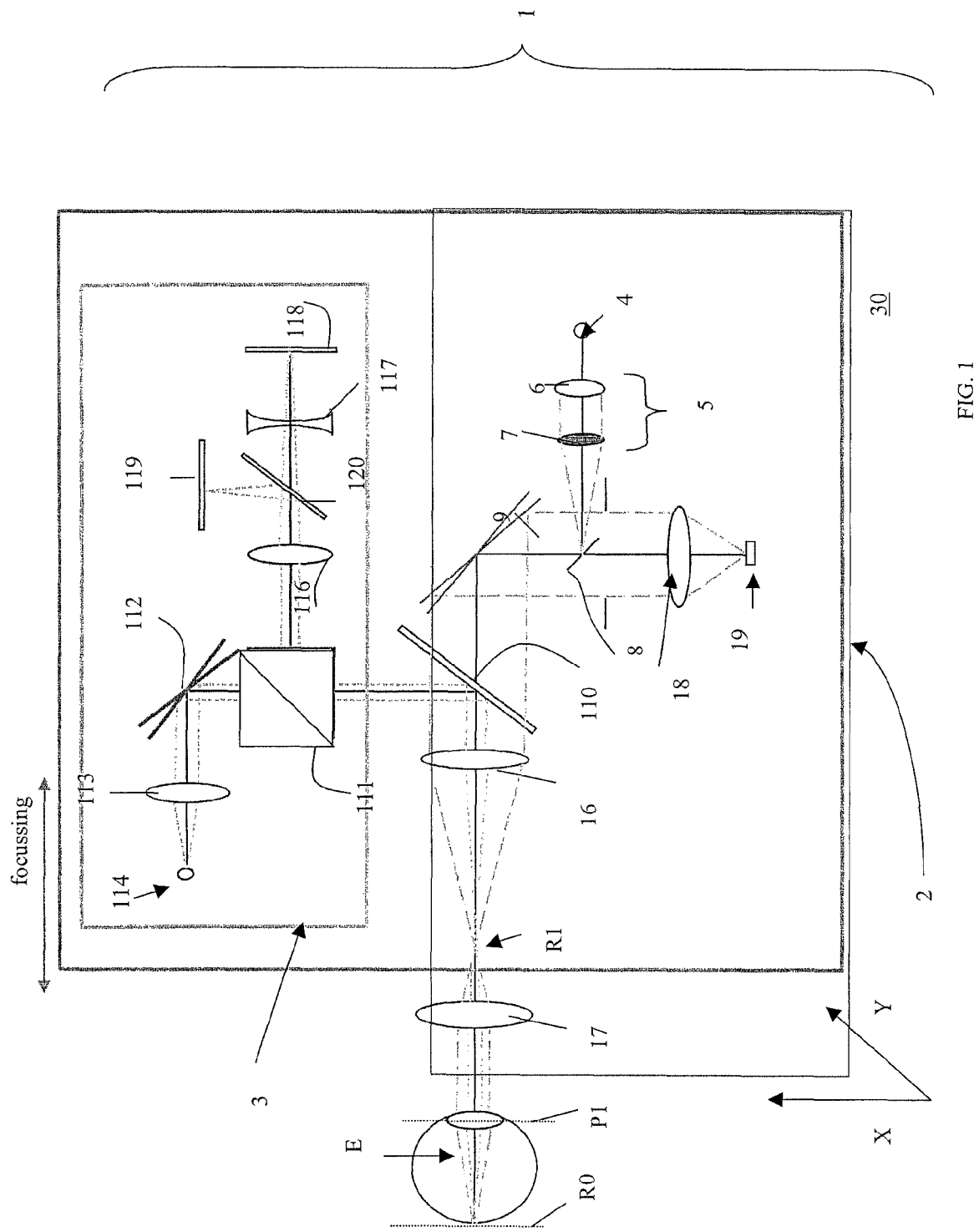
FIG. 1 is a schematic diagram of an element, an optical head, of an optical instrument for the examination of the eye according to the invention.

With reference to FIG. 1, 1 indicates an optical head of an instrument for eye examination according to the present invention. The instrument including the optical head 1 is used to examine an eye E of a patient, eye which is depicted only very schematically in FIG. 1.

The instrument further includes a control board 40 (shown in FIG. 6) and a software (see FIG. 7) executed in an appropriate computer 50, for the control of the optical head 1, as better outlined below. The software and the computer are also responsible of the communication with an operator of the instrument, via preferably a monitor or display 51 on which information relative to the performed test on the patient's eye or to the instrument status are shown.

The optical head 1 includes an imaging system 2 and a projection system 3, both controlled by the control board 40, computer 50 and software.

The imaging system 2, preferably a laser scanning imaging system, even more preferably a line laser scanning imaging system, although any other microscope might be used to obtain retina's images in the instrument of the present invention, includes a first source of light 4, which is substantially a point source of light. The light source 4 is conjugated to the retina R0 of the eye E to be examined. Preferred embodiments of the source 4 are a laser or, as in the present embodiment, a pigtailed superluminescent diode (SLD) (for example, a Superlum SLD-371). The first source of light 4 has preferably a central wavelength within the infrared (IR) range, for example at 850 nm. The selected wavelength of the light source 4 is a suitable compromise between the produced scattering (the longer the wavelength, the more the scattering because a deep light penetration into the eye's tissues takes place) and the patient's discomfort (the shorter the wavelength, the higher the probability that the patient sees the incoming light, which is an unwanted distractive effect and additionally the pupil of the patient contracts). Additionally, sensors (detectors) having a reasonable sensitivity for this application are available for infrared wavelengths, as will be clarified below.

The imaging system 2 further includes a line generator optics 5 through which the light coming from source 4 passes. In the preferred embodiment of FIG. 1, the line generator optics 5 comprises an anamorphic collimation system made of an aspheric fast lens 6 and a cylindrical lens 7. By means of the line generator optics 5, the light from source 4 is converted into a line of light, which is focused to the object to be examined, in this case the patient's eye E retina R0. The focusing on the retina is performed by a suitable optics which, in addition, scan the line of light obtained as output of the line generator optics 5 on a portion of the retina itself. In this preferred embodiment depicted in FIG. 1, the line beam of light has the shape of a line focused—along one direction—on a mirror 8, which is conjugated with the patient's cornea by means of two additional lenses 16 and 17, however any other suitable optics can be used. Lenses 16 and 17 can be considered the relay optics of the instrument of the invention.

From the mirror 8, the beam is reflected towards suitable interface means to receive the line of light and scan the same, preferably in a direction perpendicular to the line of light itself, across a portion of a patient's retina R0. For example, the suitable interface means may include a scanning mirror 9 driven by a galvanometer (not shown) which scans the line of light across an angle of interest and is conjugated with the patient's pupil P1. A suitable scanning angle on the retina ranges from 20° to 60°, more preferably 40°.

The scanning line of light on the retina is the equivalent of a scanning raster, which is then focused by the relay optics, in particular the lens 16 (which for example has a focal length of 100 mm), as already said, which is custom designed for proper aberrations correction; and at a focal length distance from the lens 16 the raster is conjugated with the retina (position R1). From position R1, the raster passes through the aspheric lens 17 and making pivot around the patient pupil P1, the line is focused on the retina R0.

The line of light is in focus on the retina in one direction whereas on the other direction is collimated. The collimated direction on the retina corresponds to a focused beam on the cornea, whereas the focused direction on the retina corresponds to a collimated beam on the cornea.

FIGS. 11a and 11b shows schematically the line of light focused on the two orthogonal planes on the cornea (FIG. 11a) and on the retina (FIG. 11b).

The illumination path including relay lenses 16 and 17 has a substantially telecentric design and the required patient's pupil is determined by the magnification given by lenses 16 and 17. The line of light then impinges on the retina R0 (or the other eye's portion under examination), where it can be either absorbed, it may be transmitted through the retina or may be reflected by the same. This returning light, then impinges on lens 17 which focus the same in position R1 and then, after passing through the lens 16, the returning light is de-scanned by the scanning mirror 9 in a synchronous manner with the incoming line of light directed towards the retina. The scanning mirror 9 directs the returning line of light from the retina so that it passes through a lens 18, potentially a linear aperture and then the line impinges on a linear detector 19. Lenses 16, 17 and 18 are apt to conjugate the line of light onto the detector 19. The detector 19 is then apt to send the collected information to the control board 40 in order to create retina's images.

More in detail, an instantaneous image of the line is produced by the lens 18 into the linear detector 19, such as a CCD linear array. According to a preferred embodiment, the linear array is an Atmel Aviiva 1024CL and lens 18 is custom designed for aberrations correction with a focal length of 60 mm. The linear CCD is conjugated with retina R0 (the CCD, due to its conformation, has also the function of linear aperture) and the system realizes a one dimensional confocal device: the retina is illuminated line by line and observed line by line. Electronic signals generated by the linear detector 19 are then preferably elaborated by a control board 40 (see FIG. 6), preferably based on a Field Programmable Gate Array (FPGA), which drives the light source 4, the scanning mirror 9 and other motion systems which will be better described below, which combines the different lines and forms an image. The image is then elaborated by the embedded software included in the instrument for eye examination of the invention and also better outlined below. The control board therefore, using the proper software and the computer 50, generates images of the retina from the acquisition of the reflected lines of light.

Figure 3:
FIG. 3 is an image of a retina obtained using the instrument of the invention of FIG. 1 or FIG. 2.
Figure 3:
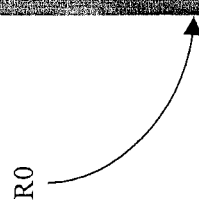

The total effect of being confocal in one direction and non-confocal in the other one yields to good image quality as reported in FIG. 3, where an image of a patient retina is shown, as obtained with the imaging system of instrument of the invention.

One advantage of the imaging system described above lies in the very small entrance pupil for the patient's eye, which allows an easy use of the instrument also in non dilated patients. The imaging and illumination pupils of the instrument are coaxial: the illumination pupil is determined by the width of the mirror 8 (in the preferred embodiment 4.5 mm) whereas the imaging pupil is given by the aperture of the scanning mirror 9 (in the preferred embodiment 10×15 mm). This leads to an imaging and illumination pupil around 3 mm and 1 mm in diameter respectively at the patient's eye. These values are smaller than the smallest typical pupil of a patient having a diameter of approx 4 mm.

The optical head 1 comprises also a projection system 3 which projects stimuli on the retina R0. These stimuli are directed to the retina R0 along a path which is for a portion in common with the optical path of the line of light generated by the imaging system 2, in particular the common path comprises the relay lenses 16 and 17, as better explained below.

The projection system 3 includes means to generate a stimulus that is projected in different positions in the retina; a uniform background which has a fixed brightness; and a fixation target that is fixed in position (i.e. it is projected always in the same retina's location) but its shape can be changed.

Different stimuli are displayed on the retina R0 in order to obtain a detailed functional mapping of the fundus of the eye E. Preferably, such a mapping emulates classic Goldmann perimetry. The stimulus is obtained using a second light source, preferably emitting visible light, such as a white LED emitting visible light, that illuminates a pinhole 114 conjugated with the retina R0. Preferably, the pinhole size is 100 μm and has been chosen to obtain a Goldmann III stimulus on the retina; it is to be understood however that any other stimulus can be obtained and it is encompassed by the present invention. Preferably, the light emitted by the second light source has a wavelength comprised in the visible range.

The rays exiting the pinhole 114 (which can be considered the point source of light, i.e. the "location" of the second light source) are collimated by means of a lens 113 (e.g. 35 mm) towards movable mirror 112, preferably a kinematic or a gimbal mounting mirror, which is positioned at a focal length distance from the lens 113. The mirror 112 has for example an aperture of 2 mm and is conjugated to the patient's pupil P1 by means of the relay lenses 16 and 17.

The stimulus projection path from the second source of light (i.e. from pinhole 114 which, as said, can be considered the location of the second source of light) to the retina is designed to be telecentric and to provide a uniform illumination not dependent on the projection angle. The small aperture in the movable mirror 112 allows very low aberrations with low cost optics and guarantees no variations in retina irradiance despite the patient pupil variations in time. In order to be telecentric, the movable mirror 112 has to be placed in such a way that it is positioned at the common focal plane of lenses 16 and 113, i.e. the rear focal plane of lens 16 has to coincide with the front focal plane of the lens 113.

Figure 1A:
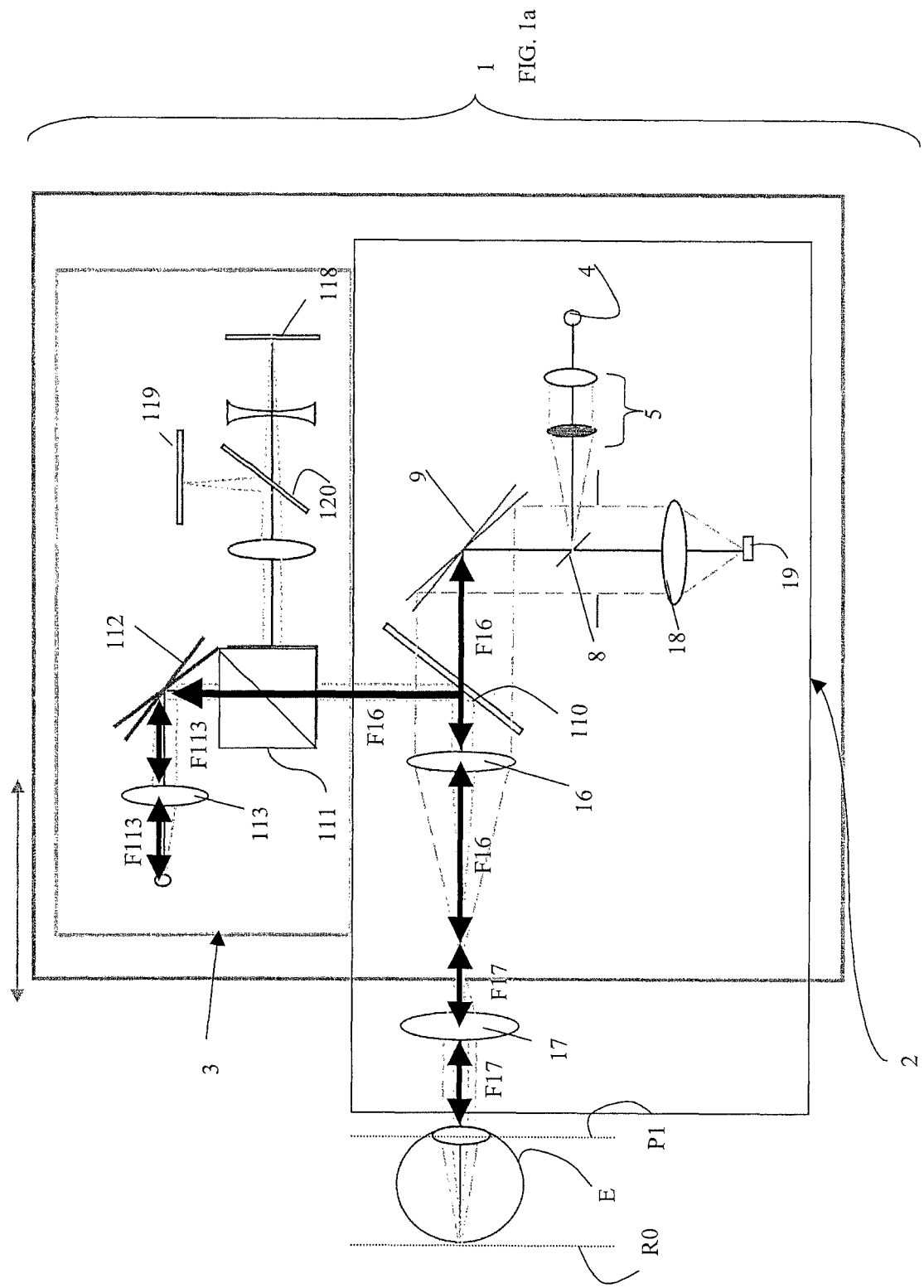
FIG. 1a is a schematic diagram showing the focal lengths and distances among lenses of the optical head of FIG. 1.

In order to obtain a telecentric design of both imaging and projection systems 2,3, the following condition should be fulfilled (see FIG. 1a).

In the imaging system 2, in order to be telecentric, the pupil P1 of the eye E is located at a focal length F17 of lens 17 distance from lens 17. The distance between the two relay lenses 16 and 17 is equal to the sum of their focal lengths F16 and F17. Additionally, the scanning mirror 9 is also at an optical distance F16 from lens 16 equal to the focal length of lens 16. In the projection system 3, to be telecentric, the movable mirror 112 is at a distance equal to focal length F16 of lens 16 from lens 16 and additionally the same mirror 112 is at a distance equal to the focal length F113 of lens 113 from lens 113. The pinhole 114 is also located at the focal length distance F113 from lens 113.

According to the invention, the projection system 3 has a telecentric design and, according to a preferred embodiment, the imaging system 2 is also telecentric.

Figure 5B:
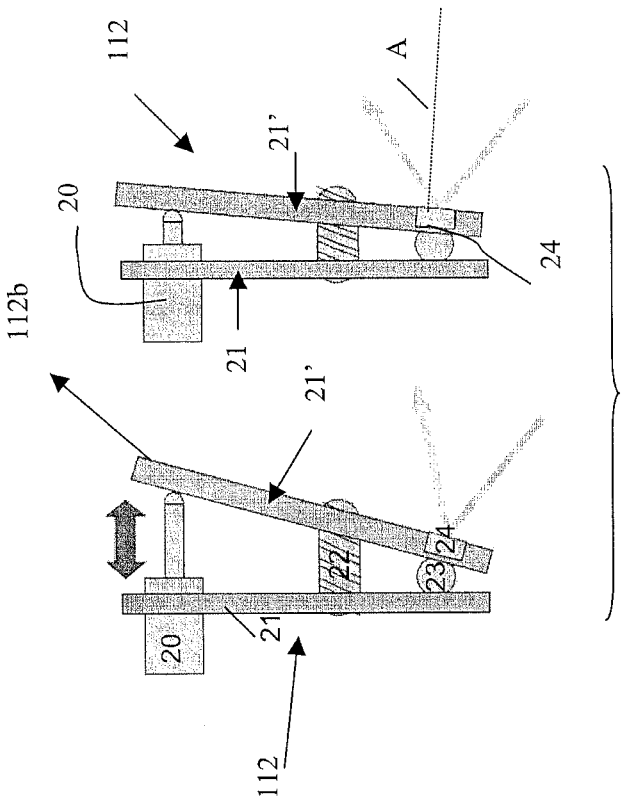
FIGS. 5a and 5b are a perspective view and lateral views, respectively, of a mirror included in the element of FIG. 1 or FIG. 2 of the instrument of the invention.
Figure 5A:
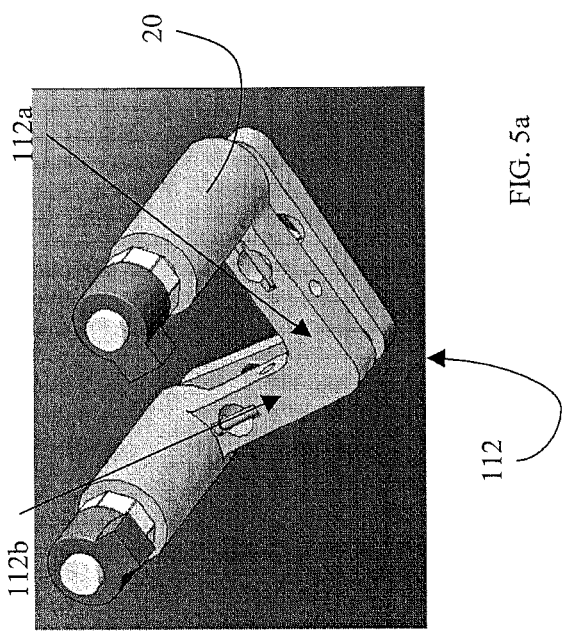

The movable mirror 112 (in FIGS. 1 and 1a mirror 112 is shown as two crossing lines in order to represent the fact that it moves) is depicted in more details in FIGS. 5a and 5b: it comprises two arms 112a, 112b that are driven by two linear stepper motors 20 (for example Haydon LC157), see FIG. 5b where only a motor is shown. The mirror 112 additionally includes a still support 21, connected by pulling springs 22 to a moving support 21'. Together with a coupling sphere 23, the two linear motors 20 push the moving support 21', counteracting the two springs 22 to equilibrium. A linear motion of one motor 20 (see FIG. 5b where two different positions of the motor 20, and consequently of the arm 112b, are depicted) causes a deflection on one arm 112a, 112b. The deflections of the two arms, i.e. their different tilting and inclination caused by the motions of the motor, are decoupled, i.e. the motions of arm 112a does not affect the motions of the arm 112b, which can be controlled substantially in an independent way.

On the intersection between the two arms 112a, 112b, the movable mirror 112 includes a deflecting mirror 24. A geometrical axis, called adjustment axis A, around which each arm performs the described motions, i.e. the movements due to the motions of the motor 20, is centered on the mirror 24. Since the adjustment axis is centered on the deflecting mirror 24, nearly pure tip or tilt of the light beam impinging the mirror 24 when adjusting a single motor are obtained. This adjustment comes without the coupled effect of displacing the beam as with conventional mirror mounts: the are only rotational movements applied to the beam exiting the pinhole 114 and focused by lens 113, and no translations of the same.

In the example, the angular resolution of the motion is 0.0285° along each axis (X,Y) which corresponds to a resolution of around 0.1° on the retina (given by the magnification of lenses 16 and 17). The mirror 24 rotates across a range of +/−1.5° to get a total projection field on the retina of about 20°.

The stimuli irradiance on the retina is controlled by the current LED using a pulse width modulation (PWM) of the current itself. In this manner the stimuli projected onto the retina can be varied.

As said, the position on which the stimulus is projected to the retina R0 is selected by the position of the movable mirror 112, which in turn implies that it depends on the position of mirror 24 on which the light exiting lens 113 impinges. The beam forming the stimulus, after having been re-directed by mirror 24 passes through a Dichroic mirror 110, such as a cold mirror (Thorlabs FM203) that reflects visible light used for retina stimulation, i.e. the light generated by the second light source 114 of the projection system 3, and transmits infrared (IR) light. The dichroic mirror 110 therefore connects the light path of the imaging system 2 beam with the light path of the projection system 3 beam.

Indeed, after having passed the dichroic mirror 110, the light forming the stimulus is focused by relay lenses 16 and 17 onto the retina R0.

In addition to the stimuli, an uniform background is also projected by the projection system 3 onto the retina. The perimetry test is indeed based on the patient's sensitivity to the contrast between the background and the stimulus, therefore the seen contrast between the projected stimulus and the projected background—as seen by the patient—is checked.

The background may be obtained for example using a third light source 119, such as preferably a flat panel made of a diffusive element transversally illuminated with LEDs, also emitting visible light. The third light source 119 is conjugated with the retina R0. The light emitted by the panel 119 is re-directed via suitable optics, such as redirecting mirror 120, lens 116 and coupling prism 111 which is used to couple the fixation and background signals, and then projected into the retina R0, always through relay lenses 16 and 17. Along the same optical path (i.e. after the redirecting mirror 120, the optical path of the background light and of the fixation target are the same), defined by the prism 111 which directs light against the dichroic mirror 110, just adding lens 117 of focal length of −35 mm (which can also be omitted), the fixation target 118 is also projected into the retina R0. The fixation target 118 is also conjugated with the retina R0 and may be produced for example by a fourth visible light source such as a LED.

Optical prism 111 is therefore used to re-direct the light coming from second, third and fourth (stimulus, background and target) light source onto the dichroic mirror 110 and then to the relay lenses 16 and 17 so that the light can be focused onto the retina R0. Indeed, light beam from all the second, third and fourth source impinges on the prism 111.

Figure 4:
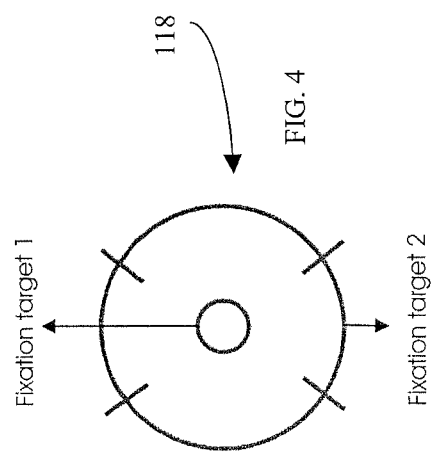
FIG. 4 is a schematic sketch of fixation targets generated and used by the instrument of the invention of FIG. 1 or FIG. 2.

Preferred embodiments of fixation targets are shown in FIG. 4: a fixation target 1 (represented as the internal circle of the figure) represents the standard target, while fixation target 2 (external circle with bars) represents the target when the target 1 is not seen, or seen with difficulties, by the patient.

The fixation target 118, as indicated by its name, is a target that the patient has to fixate while the stimuli are projected onto the retina, in order to keep the eye as still as possible (i.e. to avoid ocular movements). The position in which it has to be projected is determined by the control board 40 and it is pre-determined before the test on the patient begins.

The fixation target 118 and the background 119 are both focused onto the retina by means of the relay lenses 16 and 17.

The focusing onto the retina due to spherical defects of the patient is managed by moving the whole bench 30 of the optical head 1 with respect to lens 17 that remains fixed. This mechanism provides the advantage of having just one motor (Haydon E43H4J) moving all light sources and linear detector 19 mounted in the bench 30 accordingly while keeping the working distance between lens 17 and patient's eye E constant. In this way, the confocality between light sources and linear detector 19 is guaranteed for any spherical defect of the patient. Preferably, the corrected defects of the patient are within a range of +15 D/−15 D.

Figure 2:
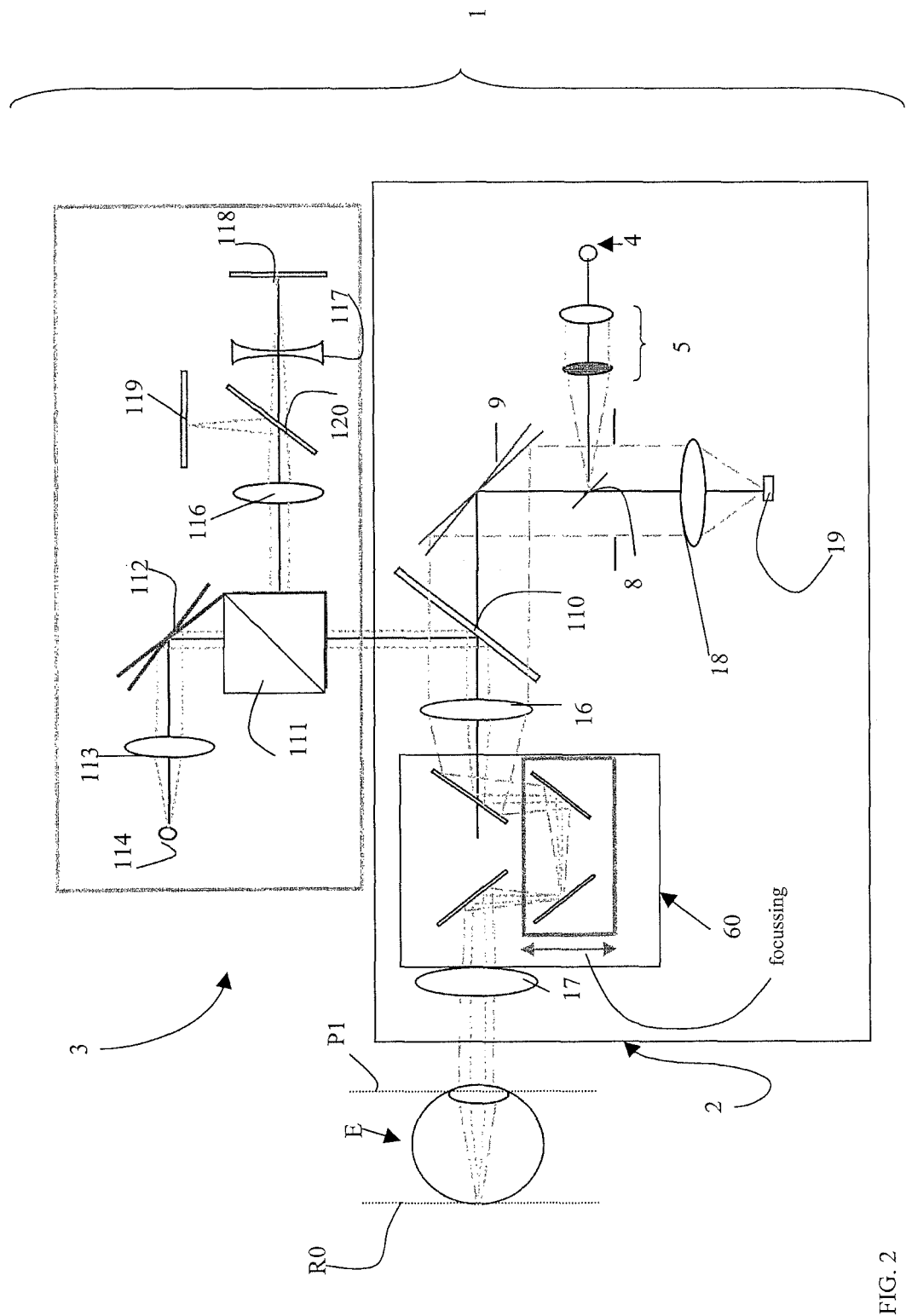
FIG. 2 is a schematic diagram of a different embodiment of the element of FIG. 1 of the instrument for the examination of the eye.

According to a different embodiment of the invention, depicted in FIG. 2 and in which the same elements of the instrument of the invention depicted in the drawing of FIG. 1 are indicated with the same reference numerals, a different system to obtain confocality between light sources (first, second, third and fourth) and linear detector 19 is employed, to correct defects of the patients' eye. The bench 30 is not moved any more as a whole, but four mirrors (called globally 60 in FIG. 2), two of which can be shifted in the directions indicated by the arrow with respect to the bench, are mounted on the bench 30 so that the distance (the optical path of the light) between relay lenses 16 and 17 can be varied.

Figure 6:
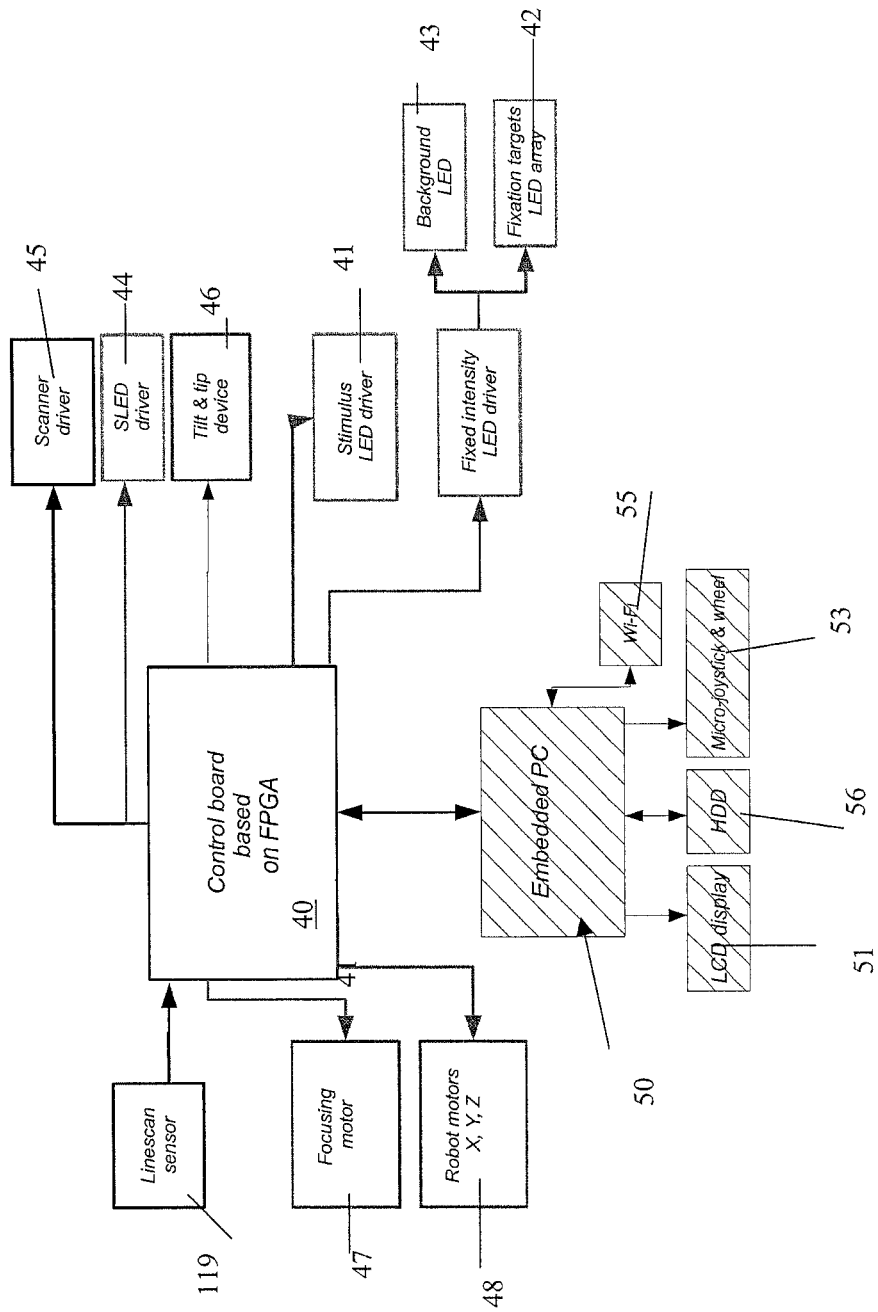
FIG. 6 is a schematic diagram of additional elements, a control board and an embedded computer, included in the instrument of the invention.

The instrument according to the invention, further includes the control board 40, schematically depicted in FIG. 6. The control board is preferably based on a FPGA and has the following functionalities.

The board 40 is apt to drive the light sources: the SLD 4 (through driver 44) and all visible LEDs used in perimetry, i.e. both the stimulus LED (driver 41), the fixation target LED (driver 42) and the background LED (driver 43) included in the panel 119.

According to an embodiment of the invention, the stimulus and background LEDs are driven by PWM at 120 Hz with 4096 levels. This guarantees a very stable irradiance on the retina given by the direct control of the LED current.

The board 40 also acquires the images from the linear CCD 19, for example using a CameraLink interface, packs the stream of signals coming from the CCD 19 in group of lines (usually 512, 1024 or 1365) and sends the result to the embedded computer 50, which is preferably also part of the instrument of the invention. This line acquisition is synchronized with the galvanometer (scanner driver 45) moving the scanning mirror 9: the board 40 provides an analogical triangular signal to the galvanometer whose amplitude and frequency determines respectively the raster amplitude on the retina and the frame frequency.

The board 40 also drives the two stepper motors 20 of the movable mirror 112 (tilt and tip device 46), the focusing motor to move the bench 30 with respect to lens 17 (driver 47, in case of embodiment of FIG. 1) and the three robot motors (motors not shown in the pictures; the driver used is driver 48) used for optical head 1 positioning.

The robot motors are used for the automatic alignment of the optical head 1: when the exam starts, the proper position of the head 1 with respect to the patient's eye E is determined by processing the retina's images obtained in the CCD 19 and a feedback is sent via the control board 40 to the robot motors. The continuous feedback to the motors during the exam guarantees a correct alignment of the optical head 1 and speeds up the perimetry exam compensating for patient movements.

The embedded computer 50 communicates with the control board 40 and hosts a perimetry software including image processing and provides an interface, such as the monitor 51, e.g. an LCD display and input devices 53 (a joystick and wheel in the example of FIG. 6) to the user. Wi-Fi functionalities 55 and a HDD 56 can be also included in the computer 50.

When the exam starts, the method of the invention includes the following steps, as depicted in FIG. 7. The software included in the instrument of the invention may be available in different versions, for example as a Basic software and an Advanced software, the upgrade from one software to the other could preferably be available for example via Internet.

The main difference between the two configurations is that the Basic software can only perform exams in Screening mode, while the Advanced software also features an Expert mode and a Follow-up mode, as detailed below.

The operator of the instrument for eye examination, for example a doctor, inserts a doctor's ID in the interface of the instrument, if such a feature is enabled. Additionally, the operator preferably inserts patient data or selects a patient from the database in case the patient has already underwent some tests with the instrument of the invention.

At installation time, the owner of the instrument can optionally configure the system so that it will ask for a login ID for each session of test. In case of multi-practitioner centers, such ID shall identify the doctor to whom the patient is linked, and not the operator.

The login management method to the software of the instrument of the invention can be changed at any time by the user, and it optionally features a password. As a preferred embodiment, the doctor ID is related to the activation in the WEB of the space provided to store exam data. Doctor ID is stored together with each exam.

The operator inserts patient data such as: name, sex, age (birth year) and race. An optional 'Patient ID' is used to solve a coincidence of names.

The instrument may be provided with a USB mini-keyboard. The keyboard can be back lighted, wireless, or both. The touch panel provides a virtual keyboard too, just in case the doctor needs to save room on the table where the unit is hosted.

In order to prepare for the test, the operator asks to the patient to take a stable position onto the patient rest, then he starts the test by manually moving the optical head 1, by means of the interface 53, such as a micro joystick, towards the eye E of the patient to be examined: as soon as the instrument, i.e. the board 40 and the software, recognizes the eye E and a given working distance range is reached, it preferably warns (acoustically and visually, on the display) the operator about the new status, it takes control over the optical head motion, and automatically aligns the optics with respect to the patient and performs the test. According to an embodiment of the invention, on the display 51*a* STOP button may appear, to allow the operator to stop motion and retake control over the software. Eye recognition (OD/OS) is automatic.

At step 1, the software included in the instrument for eye examination of the invention acquires and displays images of the retina as received from the control board 40 which has elaborated the signals coming from the CCD 19. The images are for example in digital format at 14 fps, 512×512 pixel on display, out of 1024×1024 or 1024×1348 from the camera (sensor 119). The first retina's images are most probably not clear and out of focus, the optical head 1 still have to be aligned and focused, however it is useful to have this preliminary step already visualized on display 51 to understand whether the patient needs to be moved from the current location. During the first step, the optical head reaches an alignment: the images from the optical head 1 are processed by the software to find out the correct location of the head 1 with respect to the patient's eye E and the robot motors (via driver 48) receive a feedback from the control board 40 including positioning instructions.

Once the correct working distance is determined, the focusing motors are driven (driver 47) by the control board 40 in order to make a scan over a suitable range (e.g. −15 D/+15 D) to make an automatic compensation of patient's equivalent spherical error. The Fast Fourier Transform (FFT) of the images acquired during the scan is calculated and the Power Spectral Density is chosen as the parameter to get the best point of focus. The focusing due to the patient's spherical defects represents step 2 of the method of the invention.

A set of images of the retina is acquired (step 3) via the imaging system 2, among which one is automatically chosen (at least by best focus, possibly also by crescents absence, reflexes absence, most central fixation, etc) and stored, for internal reference, and used to feed a retina tracking algorithm, detailed below.

At this point the perimetry test starts (step 4), in which the projection system 3 projects the fixation target 118 which has a predetermined shape (a circle), size (1 degree in diameter), color (red) and position (central). This fixation target is fixation target 1 of FIG. 4.

The operator asks to the patient whether the target is visible or not: in case the patient's answer is negative no, the simple central target is changed into a complex target made of a bigger circle (for example a circle 12° in diameter, with 4 segments at 45°, 3° in length of which ⅓ inside the circle). This is target 2 of FIG. 4.

The software sends an instruction to the board 40 so that an acoustic beep is emitted to signal the need for patient's attention, then along an interval of 5 seconds the patient's fixation is tracked and recorded.

The LCD display 51 preferably shows to the operator a stabilized live image of the retina, that is a live image translated according to tracking data: the fixation point is moving, and it appears on the display as a dot. Indeed, as it will be better clarified below, the patient's eye is not completely "fixed", but involuntary movements of the eye are presents, therefore these movements have to be taken into consideration.

The stimuli are then projected into the retina via the projection system 3: on the display 51, stimuli are drawn as soon as projected, and they stay on the displayed image, with a color coding indicating luminance perceived by the patient.

According to a preferred additional step of the method of the invention, for patient training before the start of the real examination, three or four "dummy" stimuli are projected, in random position but near to the center, with decreasing luminance, starting from maximum (e.g. 10000 asb) and ending to the normality threshold value. The patient's answer to such stimuli are disregarded.

During the test, the stimuli, of fixed shape (a filled circle), size (Goldmann III) and color (white) are projected according to a fixed pattern, taking in account eye movements gathered by the tracking. The fixed pattern is determined by the software.

At the same time, also the uniform background is projected on the retina.

During this step of the exam, on the live image shown to the operator in the monitor 51*a* white spot appears representing each stimulus, in the position where it has been projected (position that is determined by the software and obtained by moving movable mirror 112 accordingly), related to the retina being tracked.

The patient provides an input to the instrument by pushing a button or a pedal (cable-connected to the instrument) whenever he perceives a stimulus.

This allows a subjective measurement of differential light sensitivity seen by the patient, which is done by projecting a fixed background under a stimulus of variable intensity and position. The uniformity of the projection with respect to the angle is guaranteed by the telecentric design of the projection system 3. The stimuli can vary across a range of 34 dB: this dynamic is preferred but can be enhanced increasing the number of bits used of the PWM. For every and each of the points in the perimetry grid, the minimum differential light sensitivity is determined and registered. The average of the sensitivity values on the retina provides an index of global sensitivity: the lower the average sensitivity the more likely the presence of a pathology.

In particular, a location of the stimulus is selected from a predefined grid, and a command is sent to the kinematic mirror 112 so that the stimulus is projected exactly in that point (taking the tracking corrections due to retina's movements into consideration). After a given fixed time (e.g. 200 ms) the stimulus is switched off (not projected any more) and the response of the patient is awaited, i.e. whether she/he seems the stimulus or not.

The software automatically adapts the intensity of the projected stimuli to patient's answer, following a fixed strategy. Such a strategy for example may check the patient visual function on respect of age matched thresholds, in order to be able to classify retinal sensitivity as 'within normal limits', 'suspect' or 'outside normal limits', by composing the results from each tested point of the retina.

As said, during the exam, a tracking algorithm (step 5) included in the software within the computer 50 calculates the instantaneous linear shift (X,Y) along the two axes X and Y of the patient's retina with respect to the initial reference image captured in step 3 of the method of the invention. This linear shift (X,Y) is used to account for patient movements during projection. The stimuli grid position is in fact defined based on the reference image, but the real command to the movable mirror 112 has to be corrected instantaneously due to retinal motions. Exploiting the continuous tracking, the projection of the stimuli falls exactly where required. The tracking is based on a phase correlation algorithm where the spatial shift (X,Y) between images is calculated as a phase difference in the FFT of the images, i.e. between the live "instantaneous" image and the reference image.

In details, the algorithm measures a spatial shift (X,Y) of the live image in comparison with the reference image. The position of the stimulus is accordingly corrected: if the stimulus has to be projected in location (A,B) with respect to the reference image, due to the eye's movements of (X,Y), the kinematic mount mirror 112 will be commanded to be placed in such a position that the stimulus is projected in position (A+X,B+Y) and not (A,B). This correction is made to be sure that the projection of the stimuli is made according to a pre-defined grid. An example of the correction is given in FIG. 8.

Also, by storing the sequence of relative eye movements derived by the tracking algorithm, the software derives a fixation distribution plot: measuring fixation dispersion, it displays a fixation stability output in terms of 'stable', 'poor' or 'unstable'.

Figure 9:
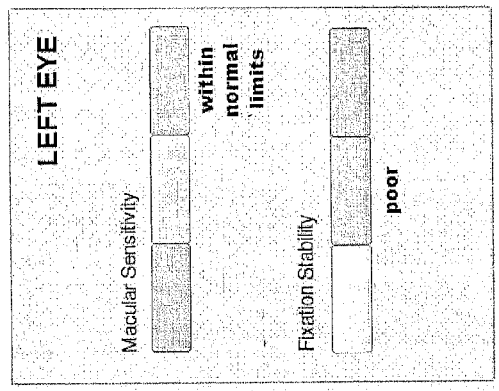
FIGS. 9 and 10 represent two interfaces displayed on a screen in the instrument of the invention and summarizing the results of a test performed with the instrument of FIG. 1 or FIG. 2.

An example of the result of the examination of the patient is displayed in FIG. 9 according to the above mentioned classification.

In the advanced version of the software, the Advanced version, an additional evaluation can be performed.

By comparing each point out of the sensitivity map obtained projecting the stimuli on the retina, with a normality database (built based on average aged-adjusted and standard deviation of the population) and by combining them, the software calculates a "retinal sensitivity index" of the examined patient.

The software derives from the sequence of eye movements a fixation distribution plot. By measuring fixation dispersion the software calculates a "fixation stability index". By comparing average position of fixation to the position of anatomical fovea, evaluated by means of image processing and statistical estimation, the software produces a "fixation location" output in terms of "superior", "inferior", "temporal-superior", "nasal-inferior", and so on.

Eventually the software processes retina image looking for non-vascular lesions (drusen, hemorrhages, exudates). Such information provides the elements for the calculation of a "morphological index".

Figure 10:
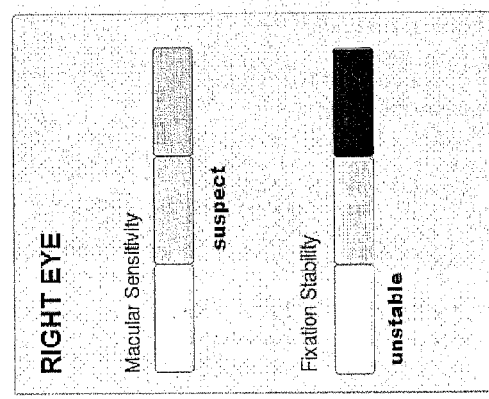
Figure 10:
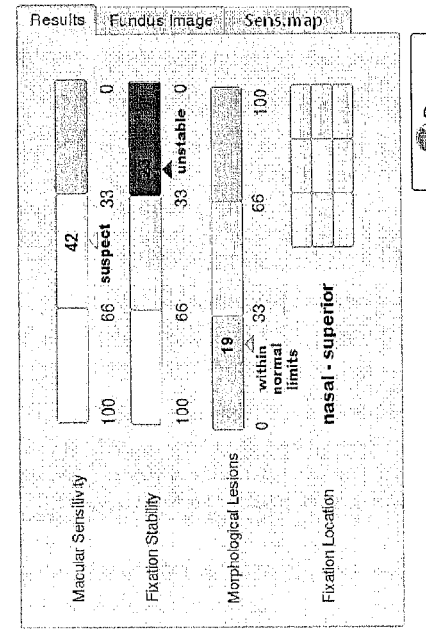

An example of an output given in this situation is depicted in FIGS. 10 and 12. Therefore, with the instrument of the invention, the following functionalities are preferably achieved:
  A. live imaging of the central retina over a preferred field of view (preferred field of view=40° in the preferred embodiment) acquired under IR illumination (preferred wavelength=850' nm in the preferred embodiment) using a confocal imaging setup;
  B. objective measurements (for example recorded at 25 Hz) of the eye movements throughout the test. This is accomplished by means of the continuous tracking performed on the live video;
  C. subjective measurement of differential light sensitivity at multiple locations in the macula, obtained as in the fundus perimetry approach.

The objective measurement of the eye movements provide information on the ability of the patient to fixate and allow to test foveal and macular integrity. The centre of gravity of the fixation points and their standard deviation is calculated: the bigger the standard deviation and the more eccentric the center of gravity the more likely is the presence of pathology.

In addition, as shown in FIG. 12, also the fixation distribution plot relative to a first interval of the test (e.g., the first 10 seconds in which only the fixation target 118 is shown to the patient and not the stimuli), called "Registration points", can be shown on the monitor 51. The average position of the registration points is also a quantity, called PRL (preferred retinal locus), of interest. "Fixation points" is the name of the fixation distribution plot relative to the whole test, which can also be displayed (see FIG. 12).

The main clinical outcome to be evaluated using the methods above is any of a series of different macular degenerations with particular interest in age-related macular degeneration (AMD) as well as amblyopia and any other condition which reduces macular sensitivity.

The exam output, displayed on the device screen, may therefore comprise all or some of the following:
  a page containing the three indexes and the fixation location information, toggled with
  the fundus image overlapped by
  the sensitivity map, overlapped by
  the fixation distribution plot, overlapped by
  a marker indicating fixation center of gravity (mean position of patient's fixation),
  a marker indicating fixation target position.

Any of the overlapped elements can be hidden interacting with the touch panel (e.g. tab-shaped buttons or radio-buttons).

Additional steps of the method of the invention may be included in case the Advanced version of the software is included in the instrument of the invention.

A follow-up step is a fully automated mode based on, and related to, a previous 'expert mode' exam.

The operator selects from the database a previous exam of the same patient. Then the exam is repeated using data gathered from previous exam in order to minimize exam time.

At the end of the exam, the software computes a differential sensitivity map, emphasizing changes statistically significant of the local sensitivity, and differential indexes.

On results page, the operator can toggle between absolute and differential values.

Also, a linear progression analysis map, showing changes sequentially overtime, is available for such follow-up exams created starting from another follow-up exam.

Data is automatically saved at the end of the exam.

Preferably, the instrument for eye examination according to the invention both stores exams into a local solid state hard disk and uploads them into a private space into the WEB.

The instrument can be preferably operated even when the internet connection is missing: in such a case, the system will store the exam in the internal HDD 56 only, and it will automatically upload it onto the WEB as soon as the connection is recovered.

The invention claimed is:

1. An instrument for eye (E) examination, said system including
  an imaging system including a first light source to produce images of a portion of said eye to be examined;
  a projection system including a second light source and a third light source to project a stimulus of visible light on a location in said portion of the eye to be examined and a background light on said portion of the eye to be examined, respectively;
wherein said projection system has a telecentric design to uniformly project said stimulus light and said background light on said portion of the eye to be examined and includes a movable mirror, comprising deflecting mirror, on which the stimulus light of said second light source impinges, said deflecting mirror rotating to redirect said stimulus light.

2. The instrument according to claim 1, wherein said portion of the eye to be examined is a portion of the retina (R0) of the eye (E).

3. The instrument according to claim 1, wherein said imaging system a linear scanning laser imaging system and said first light source is an infrared light source to illuminate said region of said eye (E).

4. The instrument according to claim 1, wherein said second light source includes a LED which emits light towards a pinhole which is conjugate with said portion of the eye to be examined.

5. The instrument according to claim 1, wherein said movable mirror is a kinematic or gimbal mounting mirror.

6. The instrument according to claim 1, wherein said movable mirror is conjugated to the eye's pupil.

7. The instrument according to claim 1, wherein said projection system has a Maxwellian design.

8. The instrument according to claim 1, including a computer system and a software, said software including a tracking algorithm to track movements of the eye to be examined around a fixed position and a compensation algorithm to move said movable mirror into the correct location for the stimulus projection taking into accounts said eye's movements.

9. The instrument according to claim 1, wherein said imaging system has a Maxwellian design.

10. The instrument according to claim 1, wherein said imaging system has a telecentric design.

11. The instrument according to claim 1, wherein said projection systems includes a fourth light source to project a fixation target on a fixed predetermined location on said portion of eye to be examined.

12. The instrument according to claim 1, including a monitor and a control board, said control board being apt to display on said monitor the result of said eye examination.

13. The instrument according to claim 1, including relay optics to focus the light emitted by any of said first, second, third or fourth light source onto said portion of the eye (E) to be examined.

14. The instrument according to claim 12, including an optical prism 111 to re-direct the light coming from second, third and fourth light source onto the relay optics so that the light is focused onto said portion of the eye (E) to be examined.

15. The instrument according to claim 2, wherein said imaging system is a linear scanning laser imaging system and said first light source is an infrared light source to illuminate said region of said eye (E).

16. The instrument according to claim 2, wherein said second light source includes a LED which emits light towards a pinhole which is conjugate with said portion of the eye to be examined.

17. The instrument according to claim 3, wherein said second light source includes a LED which emits light towards a pinhole which is conjugate with said portion of the eye to be examined.

18. The instrument according to claim 2, wherein said movable mirror is a kinematic or gimbal mounting mirror.

19. The instrument according to claim 3, wherein said movable mirror is a kinematic or gimbal mounting mirror.

20. The instrument according to claim 4, wherein said movable mirror is a kinematic or gimbal mounting mirror.

21. The instrument, according to claim 1, wherein that said movable mirror is a kinematic or gimbal mounting mirror and comprises two arms that are driven by two motors, said deflecting mirror being positioned at an intersection of said arms, said motors driving said arms around an adjustment axis (A) that is centered on said deflecting mirror.

* * * * *